United States Patent [19]

Braun

[11] Patent Number: 4,929,239

[45] Date of Patent: May 29, 1990

[54] DEVICE FOR FILLING THE MAGAZINE OF A SCALP CLIP APPLICATOR WITH C-SHAPED SCALP CLIPS

[75] Inventor: Karl Braun, Talheim, Fed. Rep. of Germany

[73] Assignee: Aesculap-Werke AG vormals Jetter & Scheerer, Fed. Rep. of Germany

[21] Appl. No.: 152,762

[22] Filed: Feb. 5, 1988

[30] Foreign Application Priority Data

Feb. 16, 1987 [DE] Fed. Rep. of Germany ....... 3704759
Sep. 19, 1987 [DE] Fed. Rep. of Germany ....... 3731613

[51] Int. Cl.⁵ .................. A63B 17/04; B65H 1/00; B31B 1/00
[52] U.S. Cl. .................... 606/142; 606/143; 227/901; 221/198
[58] Field of Search ............... 221/229, 197, 198, 287; 124/45; 128/334 R, 337, 325, 335; 227/19, 120, 901; 606/142, 143

[56] References Cited

U.S. PATENT DOCUMENTS

| | | | |
|---|---|---|---|
| 2,853,206 | 9/1958 | Uxa | 221/229 |
| 3,075,199 | 11/1960 | Rose et al. | 72/410 |
| 3,307,389 | 3/1967 | Rose et al. | 128/334 R |
| 3,410,455 | 11/1968 | Haas | 221/229 |
| 3,518,993 | 5/1967 | Blake | 227/DIG. 1 |
| 3,565,284 | 2/1971 | Hinterreiter | 221/229 |
| 3,604,425 | 9/1971 | Le Roy | 128/325 |
| 3,955,581 | 5/1976 | Spasiano et al. | 128/334 R |
| 3,958,576 | 5/1976 | Komiya | 227/DIG. 1 |
| 4,171,753 | 10/1979 | Vreede | 221/198 |
| 4,173,211 | 11/1979 | Crawford | 124/45 |
| 4,246,903 | 1/1981 | Larkin | 128/325 |
| 4,295,579 | 10/1981 | Hass | 221/197 |
| 4,311,251 | 1/1982 | Sternberg | 221/229 |
| 4,372,316 | 2/1983 | Blake et al. | 128/325 |
| 4,396,139 | 8/1983 | Hall et al. | 227/19 |
| 4,451,254 | 5/1984 | Dinius et al. | 221/198 |
| 4,564,125 | 4/1984 | Esslinger | 124/45 |
| 4,637,395 | 1/1987 | Caspar et al. | 128/334 R |
| 4,723,531 | 2/1988 | Hampton | 124/45 |
| 4,762,262 | 8/1988 | Ming | 227/120 |

Primary Examiner—Edward M. Coven
Assistant Examiner—Gary Jackson
Attorney, Agent, or Firm—Kramer, Brufsky & Cifelli

[57] ABSTRACT

For the purpose of loading the magazine of a scalp clip applicator with C-shaped scalp clips, a feed container is provided for accommodating a row of scalp clips and an insert means is arranged on the magazine for connecting the feed container with the magazine such that the scalp clips can be transferred one after the other from the feed container into the magazine.

7 Claims, 3 Drawing Sheets

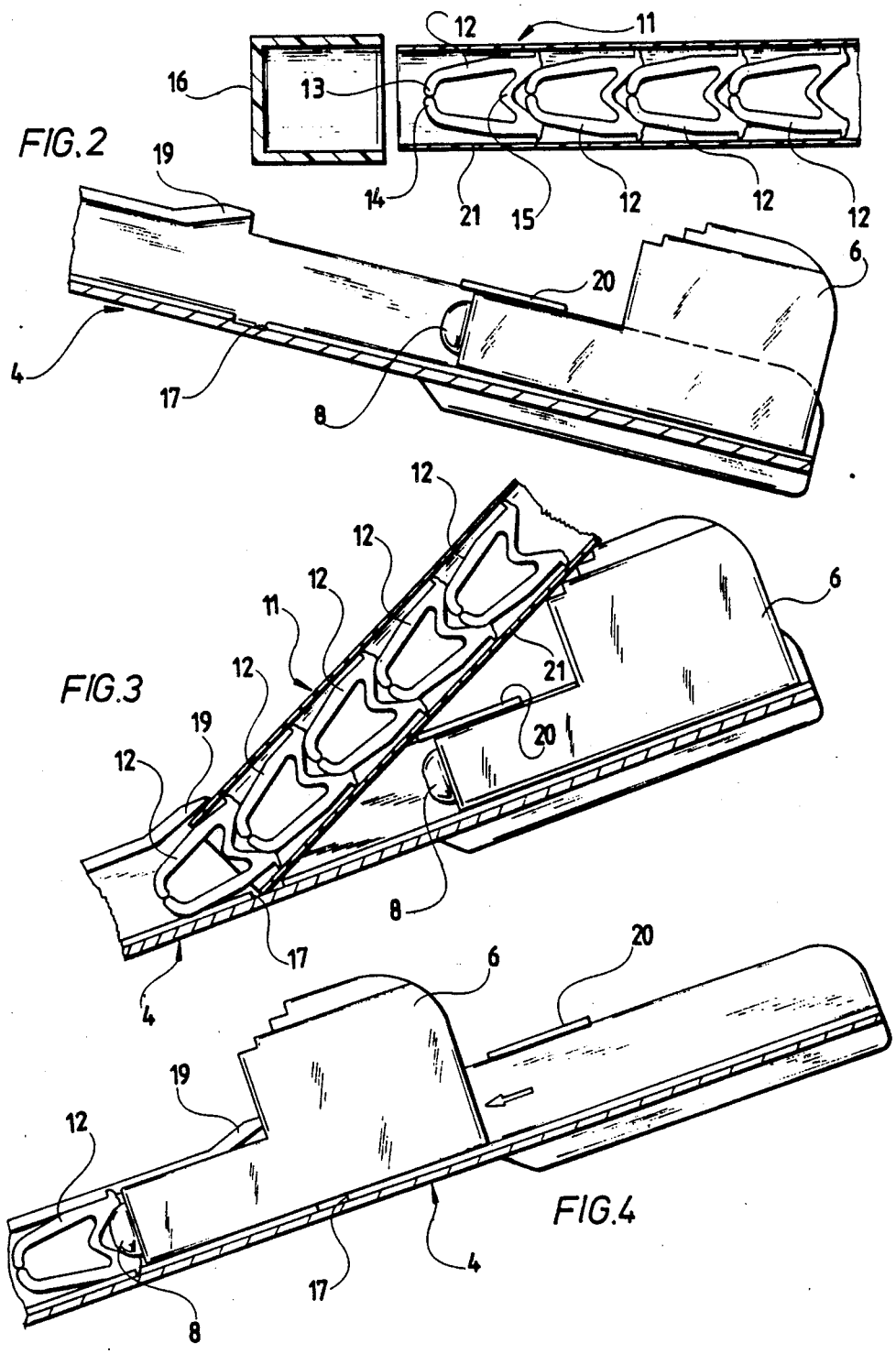

4,929,239

DEVICE FOR FILLING THE MAGAZINE OF A SCALP CLIP APPLICATOR WITH C-SHAPED SCALP CLIPS

BACKGROUND OF THE INVENTION

The invention relates to a device for filling the magazine of a scalp clip applicator with C-shaped scalp clips.

SUMMARY OF THE INVENTION

In the case of an applicator for scalp clips, such as that known, for example, from DE-PS 34 05 335, the scalp clips have to be inserted individually into the magazine by hand. This is time-consuming and requires a certain dexterity and can often not be carried out under sterile conditions.

The object of the invention is to provide a device enabling the magazine of a scalp clip applicator to be filled quickly with C-shaped scalp clips while maintaining sterile conditions. This is accomplished in that the scalp clips are arranged in a feed container in a row one behind the other, the feed container is connected to a feed opening of the magazine and the scalp clips are transferred from the feed container to the magazine without altering their sequence. The feed container can, for example, be filled with scalp clips at the factory and then delivered already sterilized. On the spot, for example in the operating theater, the scalp clips can then be transferred in the simplest manner from the container to the magazine, again under sterile conditions.

A device for carrying out the method is characterized by a feed container for accommodating a row of scalp clips and insert means provided on the magazine for connecting the feed container with the magazine such that the scalp clips are transferred from the feed container to the magazine one after the other.

It is particularly advantageous when the slide clips slide from the feed container into the magazine one after the other due to the effect of gravity.

The feed container is preferably tubular in design and closed at its front end by a cover. A preferred embodiment of an inventive device is characterized in that the insert means on the magazine has a closeable insert opening and at least one support for the feed container, whereby the insert opening can be advantageously closed by the housing of a roll spring which is mounted for displacement on the magazine.

In a preferred embodiment, the cover is articulatedly attached to the feed container and opens automatically due to interaction with the insert means when the container is fitted into the magazine.

In the preferred embodiment of the invention, the cover is biased into its closed position. The cover is advantageously provided with at least one lug and the insert means with an abutting surface for this lug such that when the container is fitted into the magazine the lug engages on the abutting surface and lifts the cover into its open position. It is favourable for the cover to be made of plastic material and be connected with the feed container via a plastic hinge integrally formed on the cover, whereby the plastic hinge can at the same time supply the biasing force for retaining the cover in its closed position.

Finally, the cover can also be pivotally mounted on the feed container by means of pivot pins.

BRIEF DESCRIPTION OF THE DRAWINGS

The following description of preferred embodiments serves to explain the invention in greater detail in conjunction with the attached drawings, in which

FIG. 2 is a part-sectional view of the applicator along line 2—2 in FIG. 1 and also shows the feed container;

FIG. 3 is a part-sectional view of the applicator with inserted feed container;

FIG. 4 is a part-sectional view of the applicator after filling with scalp clips;

DESCRIPTION OF THE PREFERRED EMBODIMENT

Figure 1:
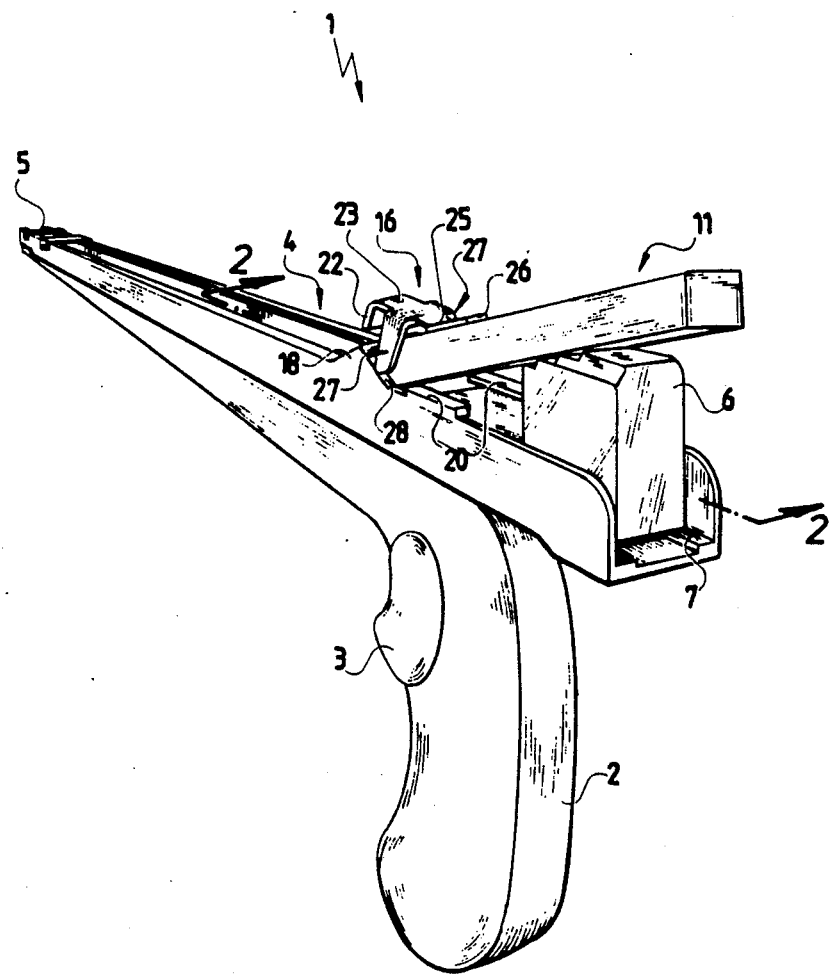
FIG. 1 is a perspective view of a scalp clip applicator with a feed container.

The scalp clip applicator 1 illustrated in FIG. 1 comprises a handle 2 and an actuating pawl 3 pivotally mounted thereon. Connected with the handle 2 is a magazine 4 projecting freely forwards and having a U-shaped cross section. This magazine holds, in a manner known per se, C-shaped scalp clips which exit individually from the front open end 5 of the magazine, when the pawl 5 is actuated, where the scalp clips can be connected with tissue parts (skin of the scalp). The scalp clips are arranged in the magazine one behind the other and are biased by a roll spring arranged at the rear end of the magazine 4 towards the open end 5 of the magazine. In FIG. 1, only a housing 6 is visible and this encloses the roll spring which rolls and unrolls in the manner of a tape measure.

The housing 6 is, as shown in the drawing, displaceable in the rearward part of the magazine in a sliding guideway 7 and can be moved back and forth between an operating position (FIG. 4) and a filling position (FIGS. 1, 2 and 3) and be secured in the respective positions.

FIG. 2 shows the rear portion of the magazine 4 with the housing 6 of the roll spring, the front end of which has a stop 8 which is displaceable under spring pressure. A feed container 11 accommodates the scalp clips to be loaded into the magazine in a row one after the other. Each scalp clip 12 comprises a pair of clamping jaws 13, 14 abutting resiliently against one another and a curved bridge 15 connecting the clamping jaws. The clamping jaws of each successive scalp clip engage in the rear curvature of the bridge of the preceding scalp clip so that the clips are tightly packed in a row one behind the other in the magazine. The arrangement of the scalp clips 12 in the feed container 11 is the same as that in which the scalp clips are intended to be found after insertion into the magazine 4. The feed container 11 may be closed by an attachable cover 16. Container 11 and cover 16 are tubular in design and have a square or rectangular cross section. The scalp clips 12 are sterilized when loaded into the feed container 11 which is subsequently closed by the cover 16.

An insert means for the feed container 11 is provided on the magazine 4. This comprises a recess 17 in the bottom of the magazine 4 and two wall portions 18, 19 which are directed upwards in the shape of a funnel and are bent inwardly at an angle. The dimensions are such that the feed container 11, once the cover 16 has been removed, can be inserted with its open end between the wall portions 18, 19 and the recess 17 so as to be self-holding. The lower wall 21 of the feed container 11 hereby rests on two flanges 20 which form a support and project inwardly from the side walls of the magazine 4. Moreover, the lower wall 21 of the container 11 can also rest on the outer surface of the housing 6. Altogether, the feed container 11 is in any case firmly connected with the magazine 9 via the insert means described.

The mutual connection between magazine 4 and feed container 11 is first made in the position shown in FIG. 2 where the magazine 4 is inclined slightly upwards and the feed container 11 is held essentially horizontal so that the scalp clips 12 cannot slide out of the container. Once the container 11 has been inserted into the magazine 4, this can be inclined as shown in FIG. 3, whereby the scalp clips 12 slide out of the container 11 into the magazine 4, without altering their sequence or separating from one another, until the magazine is completely filled.

Once the container 11 has been emptied it is withdrawn from the insert means on the magazine 4. Subsequently, the housing 6 is moved from the position shown in FIGS. 2 or 3 into the position of FIG. 4 and then secured in place. This means that the rear feed opening of the magazine which is formed by the insert means is closed and so the scalp clips 12 cannot fall out. The stop 8 connected with the roll spring contained in the housing 6 can now abut on the rearmost scalp clip 12 and bias the entire row of scalp clips towards the front open end 5 of the magazine 4 due to the pressure exerted by the roll spring and so the clips can exit one after the other when the pawl 3 is actuated.

Figure 5:
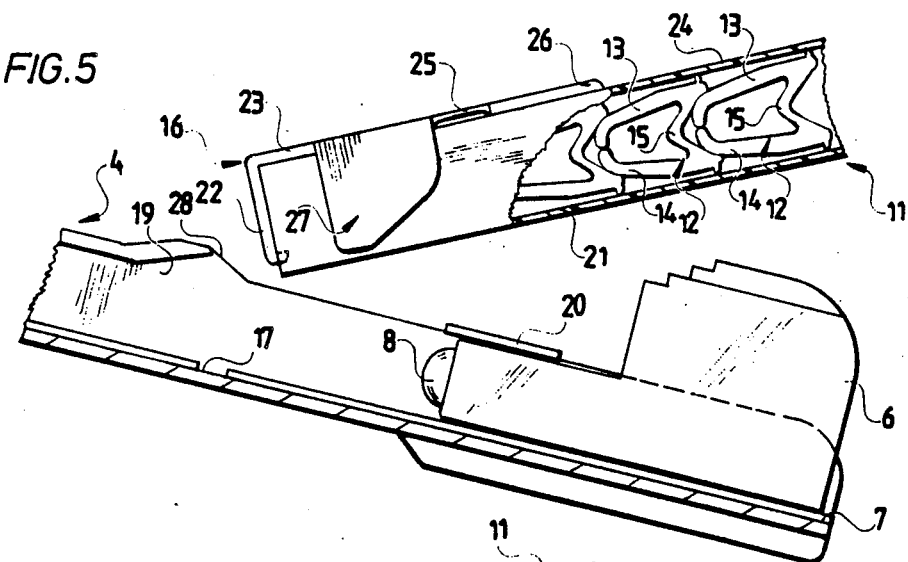
FIG. 5 is a part-sectional view, similar to FIG. 2, of the applicator with a closed container comprising a hinged cover.
Figure 6:
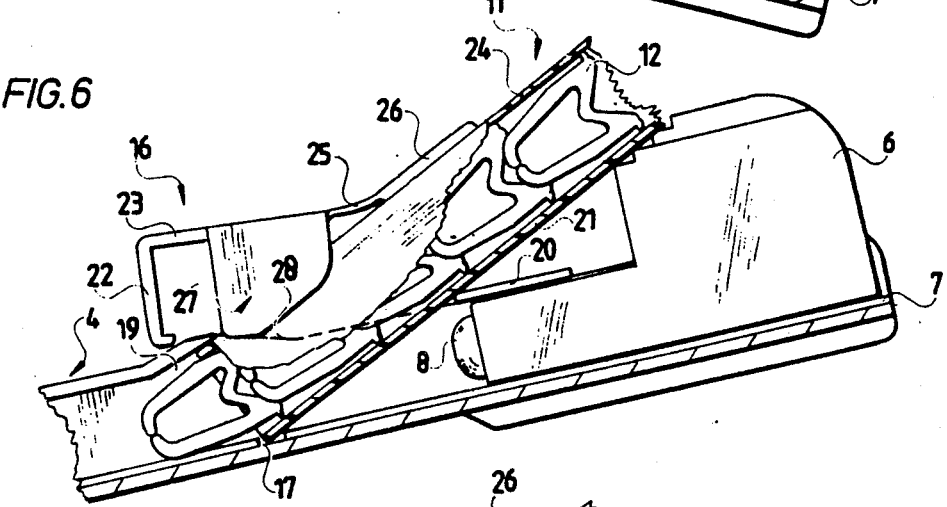
FIG. 6 is a part-sectional view of the applicator of FIG. 5 with an opened feed container and FIG. 7 is a part-sectional view similar to FIG. 6 of a modified embodiment of a feed container.
Figure 7:
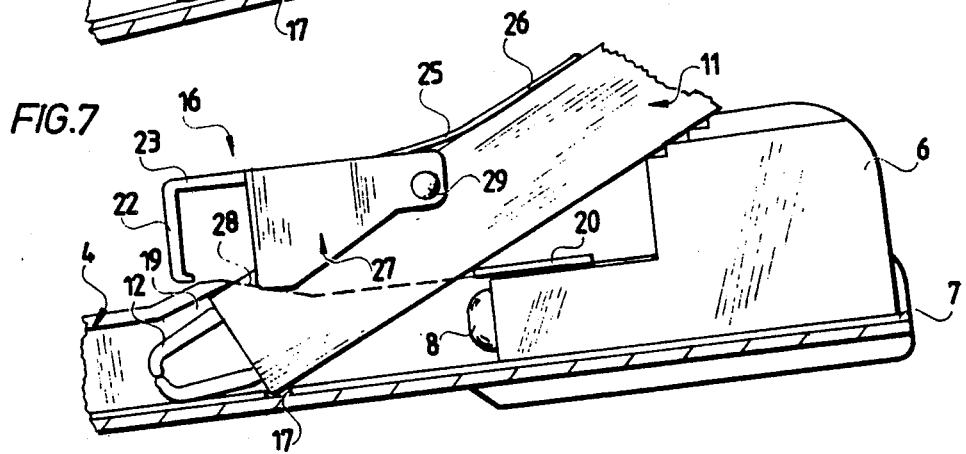

In the embodiment illustrated in FIGS. 5 to 7, the feed container 11 can be closed by a cover 16 which is articulatedly connected to the feed container 11. The cover 16 has a closure member 22 for closing the end opening of the feed container 11. A wall portion 23 of the cover 16 rests on the upper wall 24 of the container 11. The cover 16 is made from plastic and integrally connected with a plate 26 via a plastic hinge 25. This plate 26 is rigidly connected, for example adhered, to the upper wall 24 of the container 11 such that the cover 16 (cf. FIG. 6) can be opened upwardly in order to release the outlet opening of the feed container 11.

Two lugs 27 extend laterally from the upper wall portion 23 of the cover 16. These have the shape shown in the drawings and each extends along a side wall of the container 11.

Abutting surfaces 28 are provided on the wall portions 18, 19. These surfaces extend downwardly and are inclined towards the back. When the container is introduced into the insert means these abutting surfaces interact with the lugs 27 such that the lugs 27 slide upwards along these surfaces 28. The cover 16 is then automatically opened and so the outlet opening in the end face of the container 11 is free and the scalp clips 12 can slide out of the container 11 and into the magazine 4, without altering their sequence and without separating from one another, until the magazine is completely filled.

FIGS. 5 and 6 also show that the cover 16 only reaches the position in which is it fully opened when the container 11 is correctly inserted into the magazine 4. This means that the scalp clips 12 cannot exit from the container prematurely.

FIG. 7 shows a modified embodiment which essentially differs from the embodiment of FIGS. 5 and 6 in that the cover 16 has a pair of inwardly projecting pivot pins 29 in addition to the plastic hinge 25. These pins engage in corresponding openings in the side walls of the feed container 11 so that the cover 16 is mounted on the container 11 for pivoting movement.

The cover 16 is, preferably, constantly biased into its closed position by a spring so that the scalp clips 12 cannot slide inadvertently out of the container 11. The biasing force required for this can be supplied in a simple manner by the plastic hinge 25 which is of a corresponding design. It is also possible to provide a coil spring, e.g. made of plastic, on top of the feed container 11, the free end of this spring pressing on the upper wall portion 23 of the cover 16 and keeping the latter in its closed position.

What is claimed is:

1. A device for filling the magazine of a scalp clip applicator with C-shaped scalp clips, comprising:
   a feed container (11) for accommodating a row of scalp clips (12);
   a scalp clip applicator (1) having a magazine (4) adapted to hold C-shaped scalp clips;
   insert means (17, 18, 19, 20) provided on the magazine (4) for connecting the feed container with the magazine such that the scalp clips can be sequentially transferred from the feed container to the magazine, the insert means (17, 18, 19) on the magazine (4) forming a closeable insert opening;
   at least one support (20) being formed on the magazine for supporting the feed container (11); and
   a roll spring enclosed within a housing (6), said housing being mounted for displacement on the magazine (4) whereby the insert opening (17, 18, 19) can be opened and closed.

2. A device for filling the magazine of a scalp clip applicator with C-shaped scalp clips, comprising:
   a feed container (11) for accommodating a row of scalp clips (12);
   a scalp clip applicator (1) having a magazine (4) adapted to hold C-shaped scalp clips;
   insert means (17, 18, 19, 20) provided on the magazine (4) for connecting the feed container with the magazine such that the scalp clips can be sequentially transferred from the feed container to the magazine;
   said feed container (11) being tubular in design and having a front end with an opening therein;
   a cover (16) for closing the feed container; and
   means attaching the cover (16) to the feed container (11) for opening the cover automatically through interaction with the insert means when the feed container is fitted into the magazine (4).

3. The device as claimed in claim 2, comprising:
   means connected to said cover (16) for biasing said cover into position to close the front end of the container.

4. The device as claimed in claim 2, comprising:
   the cover (16) being provided with at least one lug (27);
   the insert means being provided with an abutting surface (28) for coacting with said at least one lug such that when the container (11) is fitted into the magazine (4), the lug (27) engages the abutting surface (28) and lifts the cover (16) into position to open the front end of the container.

5. The device as defined in claim 2, comprising
the cover (16) being made of plastic material; and
the means for attaching the cover with the feed container (11) being a plastic hinge (25) integrally formed on said cover.

6. The device as defined in claim 5, wherein the plastic hinge (25) supplies the biasing force for retaining the cover (16) in its closed position.

7. The device as defined in claim 2, comprising:
pivot pins (29) for pivotally mounting the cover (16) on the feed container (11).

* * * * *